(12) United States Patent
Hudson et al.

(10) Patent No.: US 7,282,044 B2
(45) Date of Patent: Oct. 16, 2007

(54) PORTABLE ENTERAL FEEDING APPARATUS

(75) Inventors: Joseph A. Hudson, O'Fallon, MO (US); Ricky A. Sisk, Washington, MO (US)

(73) Assignee: Sherwood Services AG (CH)

( * ) Notice: Subject to any disclaimer, the term of this patent is extended or adjusted under 35 U.S.C. 154(b) by 85 days.

(21) Appl. No.: 10/485,757

(22) PCT Filed: Mar. 18, 2003

(86) PCT No.: PCT/US03/08081

§ 371 (c)(1),
(2), (4) Date: Feb. 3, 2004

(87) PCT Pub. No.: WO2004/082560

PCT Pub. Date: Sep. 30, 2004

(65) Prior Publication Data

US 2005/0224534 A1    Oct. 13, 2005

(51) Int. Cl.
A61M 5/32 (2006.01)

(52) U.S. Cl. .................................................. 604/174

(58) Field of Classification Search ............... 604/174, 604/19, 118, 179, 131, 408, 345, 403; 607/153; 224/633, 235, 630

See application file for complete search history.

(56) References Cited

U.S. PATENT DOCUMENTS

| | | | |
|---|---|---|---|
| 4,386,642 A * | 6/1983 | Durbin ...................... 190/110 |
| 4,582,508 A | 4/1986 | Pavelka |
| 4,666,432 A | 5/1987 | McNeish |
| 4,799,923 A * | 1/1989 | Campbell ................... 604/179 |
| 4,998,653 A * | 3/1991 | LaBelle ....................... 224/578 |
| 5,048,512 A * | 9/1991 | Turner et al. ............... 128/876 |
| 5,168,892 A * | 12/1992 | Sunderland .................. 137/343 |
| 5,170,817 A | 12/1992 | Sunderland |
| 5,236,004 A | 8/1993 | Sunderland et al. |
| 5,250,027 A | 10/1993 | Lewis et al. |
| 5,271,745 A * | 12/1993 | Fentress et al. ............. 604/179 |
| 5,370,622 A | 12/1994 | Livingston et al. |
| 5,411,484 A | 5/1995 | Shattuck ...................... 604/179 |
| 5,478,211 A * | 12/1995 | Dominiak et al. .......... 417/234 |
| 5,614,412 A | 3/1997 | Smith et al. ............. 435/305.1 |
| 5,676,294 A | 10/1997 | Eklund et al. |
| 5,700,257 A * | 12/1997 | Minick et al. .............. 604/408 |
| 5,755,698 A | 5/1998 | Kagan |
| 5,799,846 A | 9/1998 | Pfleger |
| 6,230,952 B1* | 5/2001 | Jupiter ....................... 224/655 |
| 6,544,232 B1* | 4/2003 | McDaniel ................... 604/174 |

* cited by examiner

FOREIGN PATENT DOCUMENTS

GB    2 361 174 A    10/2001

Primary Examiner—Nicholas D. Lucchesi
Assistant Examiner—Christopher Koharski
(74) Attorney, Agent, or Firm—Edward S. Jarmolowicz, Esq.

(57) ABSTRACT

A portable enteral feeding apparatus (20) facilitates ambulatory enteral feeding and prevents damage to an enteral feeding tube during use. The apparatus includes a backpack type enteral feeding support, a soft pouch (38) having a hook and loop surface on the pouch and a rigid spacer (68). The pouch surrounds the fluid container (42), trapping and attaching it to the inside of a backpack using hook and loop system. The soft sided pouch provides easy removal and replacement of a variety of fluid containers in a mobile backpack. The rigid spacer supports the pouch and provides clearance for connection to enteral feeding tubing (32). Shoulder straps (26) substantially immobilize the apparatus relative to a subject. A telescopic enteral feeding tube concealment belt (30) is provided that allows patient mobility while concealing and protecting enteral feeding tubes.

3 Claims, 8 Drawing Sheets

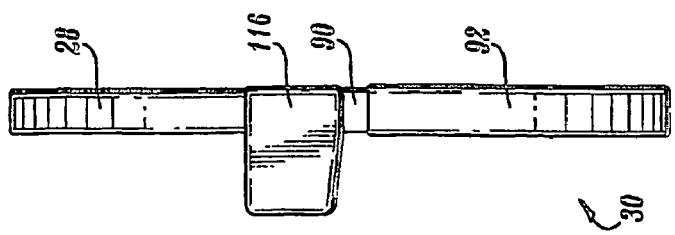
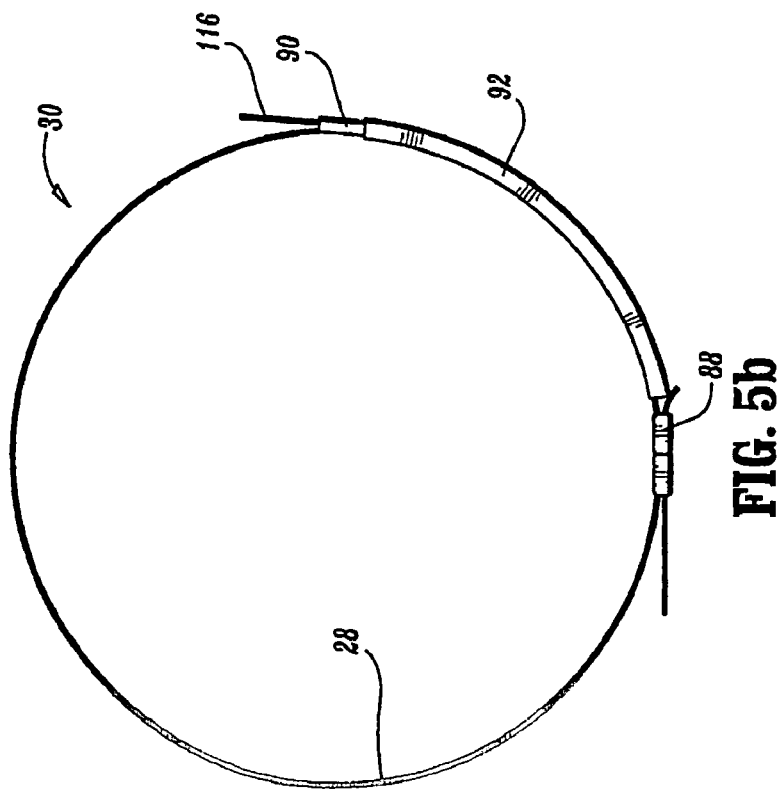
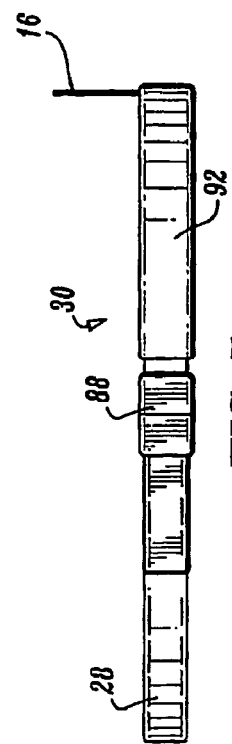

PORTABLE ENTERAL FEEDING APPARATUS

BACKGROUND

1. Technical Field

The present disclosure relates generally to enteral feeding apparatus, and more particularly to a portable enteral feeding apparatus that may be employed with alternately configured enteral feeding containers.

2. Description of the Related Art

Enteral feeding devices are used for administration of fluids to an abdominal cavity of a subject. Typically, enteral feeding devices include a feeding tube connected to a feeding container. The feeding tube allows the feeding container to be placed in an elevated location, such as, for example, on an infusion pole to facilitate gravity feeding. Some enteral feeding systems include a pump connected between the feeding container and the abdominal cavity to provide a predetermined fluid pressure in the tube. This facilitates a predetermined fluid flow rate. Many of these devices are cumbersome and unsuitable for ambulatory use.

Various known carrying devices and intravenous stands have been employed that support enteral feeding devices to facilitate ambulatory enteral feeding. These types of carrying devices and stands are often unstable and not suitable for use with non-smooth surfaces, such as, for example, sidewalks, stairs, etc.

Ambulatory support devices for fluid delivery systems are known. These devices, however, can suffer from various drawbacks. For example, these devices may include tubing that extend from an ambulatory carrying apparatus to a patient's abdominal cavity that is unprotected and susceptible to kinking or entanglement with external objects, such as, for example clothing. Such entanglement, kinking, etc. can result in damage of the tubing. Further, the tubing may be caused to inadvertently disengage from the patient's body or the feeding container. These undesirable conditions can also create a hazardous condition for a patient. For example, strain on the tubing can cause discomfort, irritation, infection or even injury.

Attempts have been made to overcome the above drawbacks by securing the tube to the patient's body or clothing using adhesive tape. This remedy however, is ineffective because the tape must be frequently removed for maintenance, etc. This compromises the adhesive quality and causes substantial pain and irritation to the patient.

The enteral feeding devices also suffer from various disadvantages. For example, some of these devices are not immobilized against a subject. Movement of the pumps and enteral feeding containers relative to the subject can strain or crimp the tubing and cause irritation and/or injury to the patient. Some enteral feeding devices include handles that are inadequate for comfortably carrying the weight of the apparatus.

Another drawback is difficulty in replacing feeding containers. Patients may suffer limited manual dexterity and have difficulty manipulating the various fasteners and container attachments. Still another drawback is aesthetic appearance. Often, the feeding container is worn in open view where tubing can be unsightly or embarrassing for the patient.

Therefore, it would be desirable to overcome the disadvantages and drawbacks of the prior art with a portable enteral feeding apparatus having an ergonomic design to facilitate use by a patient and that may be employed with alternately configured enteral feeding containers. It would be desirable if the portable enteral feeding apparatus included a removable pliable pouch that is configured to support the enteral feeding containers. It would be highly desirable if the apparatus includes a backpack for supporting the pouch and a telescoping belt apparatus that supports a feeding tube during use. Such a backpack is designed for comfortable attachment to a patient. It would also be desirable if the enteral feeding apparatus and its constituent parts are easily and efficiently manufactured and assembled.

SUMMARY

Accordingly, a portable enteral feeding apparatus is provided having an ergonomic design to facilitate use by a patient and that may be employed with alternately configured enteral feeding containers. The portable enteral feeding apparatus includes a removable pliable pouch that is configured to support alternately configured enteral feeding containers. Most desirably, the portable enteral feeding apparatus includes a backpack for supporting the pouch. Such a backpack is designed for comfortable attachment to a patient. The portable enteral feeding apparatus is easily and efficiently manufactured and assembled. The present disclosure resolves related disadvantages and drawbacks experienced in the art.

The present disclosure provides, among other things, a soft-sided enteral feeding container restraint including a soft pouch, a pouch flap, and a hook and loop surface bonded to one side of both the pouch and pouch flap. The pouch surrounds the fluid container, trapping and attaching it to the inside of a backpack using a hook and loop system. The hook and loop side of the restraint pouch is pressed against a corresponding hook and loop surface inside the backpack. The hook and loop system allows the restraint pouch to be easily loaded into the backpack and removed for cleaning.

In an ambulatory application, the enteral feeding apparatus includes a backpack holding a feeding fluid container at an elevated level relative to the location where a feeding tube enters a patient's body. The backpack configuration can thereby provide gravity assisted fluid flow without requiring a fluid pump. In some embodiments, the gravity assisted configuration for ambulatory feeding eliminates the substantial weight of a fluid pump from the apparatus. The exemplary backpack configuration also distributes weight evenly on the shoulders of an ambulatory patient. Thus, the backpack-type configuration typically requires much less effort for a patient to transport than a suitcase-type configuration, whether or not a fluid pump is used.

In one particular embodiment, in accordance with the principles of the present disclosure, a portable enteral feeding apparatus is provided. The portable enteral feeding apparatus includes a body including a flap extending therefrom. The body has an inner surface that defines a cavity such that the flap is movable to enclose the cavity of the body. A pouch is disposed within the cavity of the body and defines at least one pliable compartment configured to support an enteral feeding container. The pliable compartment is adaptable to accept a variety of enteral feeding containers. The pouch further defines an outer surface that mounts to the inner surface of the body. The pouch may include an opening to accept the neck of a variety of enteral feeding containers.

The pouch may have a tube restraining strap extending from the outside surface proximate to the opening thereof. A feeding tube is mountable to the neck of an enteral feeding container extending through the opening and retainable by engagement of the tube retaining strap to a fitting, including a flange, mounted to an end of the tube. The body includes an outer surface that may include an orifice disposed therein for placement of an enteral feeding tube. A belt apparatus may be attached to the outer surface to provide support for the enteral feeding tube.

The portable enteral feeding apparatus may include a rigid support disposed in a cavity below the pouch. The rigid support may define a cavity to provide a clearance space for an enteral feeding tube connection to the enteral feeding container. The rigid support can include a top surface having an opening defining a passageway communicating with the clearance space for disposal of a neck of the enteral feeding container.

The rigid support can include an orifice alignable with an orifice in the body for disposal of an enteral feeding tube. The portable enteral feeding apparatus may include a pump compartment extending from the body for support of an enteral feeding pump. A ductway may be disposed in the outer surface of the body. The pump compartment may have an outer surface that defines a cavity such that a flap thereof is movable to enclose a pump cavity of the pump compartment. The ductway can provide an opening between the pump compartment and the clearance space of the rigid support.

Alternatively, the body includes shoulder straps having attachment points to the outer surface of the body. The shoulder straps can be adjustable for securely mounting the body against the back of a subject.

The portable enteral feeding apparatus advantageously provides lower cost and increased flexibility to handle a variety of different feeding containers. The portable enteral feeding apparatus provides a desirable appearance to conceal the presence of a feeding device.

In accordance with the principles of the present disclosure, the portable enteral feeding apparatus may be employed with a belt apparatus is adapted for use therewith, having an orifice and an enteral feeding tube extending therefrom. Desirably, the belt apparatus includes first and second telescoping members that conceal the feeding tube while preventing hazards to the patient.

The present disclosure provides, among other things, a telescopic enteral feeding tube concealment belt that allows patient mobility while concealing and protecting the enteral feeding tubes. The telescopic concealment belt includes a stationary belt section, a telescoping belt section and a hook and loop attachment. The hook and loop attachment is disposed on one end of the stationary belt section and is mountable to an enteral feeding apparatus. The telescoping belt section and stationary belt section are slidably engaged, one within the other to form a duct having an adjustable length that supports and conceals an enteral feeding tube. A waist belt engages either or both belt sections and/or the enteral feeding apparatus to substantially immobilize the belt sections against the subject.

The belt sections may be made of a flat nylon flaps that are folded over upon themselves to form a duct shape. The belt sections are retained in a duct shape by means of a hook and loop strips bonded to the nylon flaps. One duct shaped belt section slides inside of the other forming a telescoping duct that will adjust to fit the users waist. The stationary belt section has a concealment flap extending from one of the nylon flaps. The concealment flap attaches to and conceals the access port of the backpack type enteral feeding container.

The concealment belt can further attach to an enteral feeding apparatus by the waist belt passing inside the duct and through restraining belt loops that extend from the enteral feeding apparatus. The waist belt attaches to itself at each end by any conventional buckle. Alternatively, conventional belt loops can be provided on outside surfaces of one or both belt sections for disposal of the conventional waist belt.

The belt apparatus includes a belt having a first and second end that are attachable. A first member is supported with the belt and has a first end and a second end. The first member defines a cavity that supports the belt. The first end of the first member is mountable to the enteral feeding device and the second end of the first member is configured for disposal of the tubing supported within the cavity of the first member.

The first member may include an outer flap foldable around an inner flap and releasably securable to the inner flap to form the cavity in the first member. Releasably securable attachment between the inner and outer flaps can be provided by a hook and loop strip disposed along a back edge of the inner flap releasably attachable to a cooperative hook and loop strip disposed along a front edge of the outer flap. The first member may include a concealment flap releasably attachable to the portable enteral feeding apparatus by hook and loop strips disposed on the concealment flap releasably attachable to cooperating hook and loop strips disposed on the surface of the portable enteral feeding apparatus adjacent to the orifice. The concealment flap can conceal the orifice and the proximal end of the enteral feeding tube when the concealment flap is attached to the portable enteral feeding apparatus. The hook and loop strip disposed on the concealment flap can optionally be formed as a unitary extension of the hook and loop strip disposed along the front edge of the outer flap.

The second member has a first end and a second end defining a cavity that supports the first member for movement relative thereto. The first end of the second member is configured for disposal of the first member. The second end of the second member is configured for disposal of the tubing, The second member may include an outer flap foldable around an inner flap and releasably securable to the inner flap to form the cavity in the second member. Releasably securable attachment between the inner and outer flaps is provided by a hook and loop strip disposed along a back edge of the inner flap releasably attachable to a cooperative hook and loop strip disposed along a front edge of the outer flap. The second member can be telescopically extended and retracted relative to the first member by sliding of the first member in the cavity of the second member.

In an alternate embodiment, the first member and second member are attached to the belt via belt-loops disposed on the outside surface of the first and/or second member.

In another embodiment the present disclosure, a method of supporting an enteral feeding tube in a portable enteral feeding apparatus is provided including the steps of folding an inner flap of a first member over a proximal section of a feeding tube; folding an outer flap of the first member over the inner flap of the first member and releasably securing the outer flap thereto; releasably securing a concealment flap portion of the first member to the portable enteral feeding apparatus; folding an inner flap of a second member over the first member and the feeding tube; folding an outer flap of the second member over the inner flap of the second member, and releasably securing the outer flap of the second member to the inner flap of the second member.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

FIG. 5 is an orthographic view of the belt apparatus in accordance with the principles of the present disclosure;

DETAILED DESCRIPTION OF THE EXEMPLARY EMBODIMENTS

Figure 1:
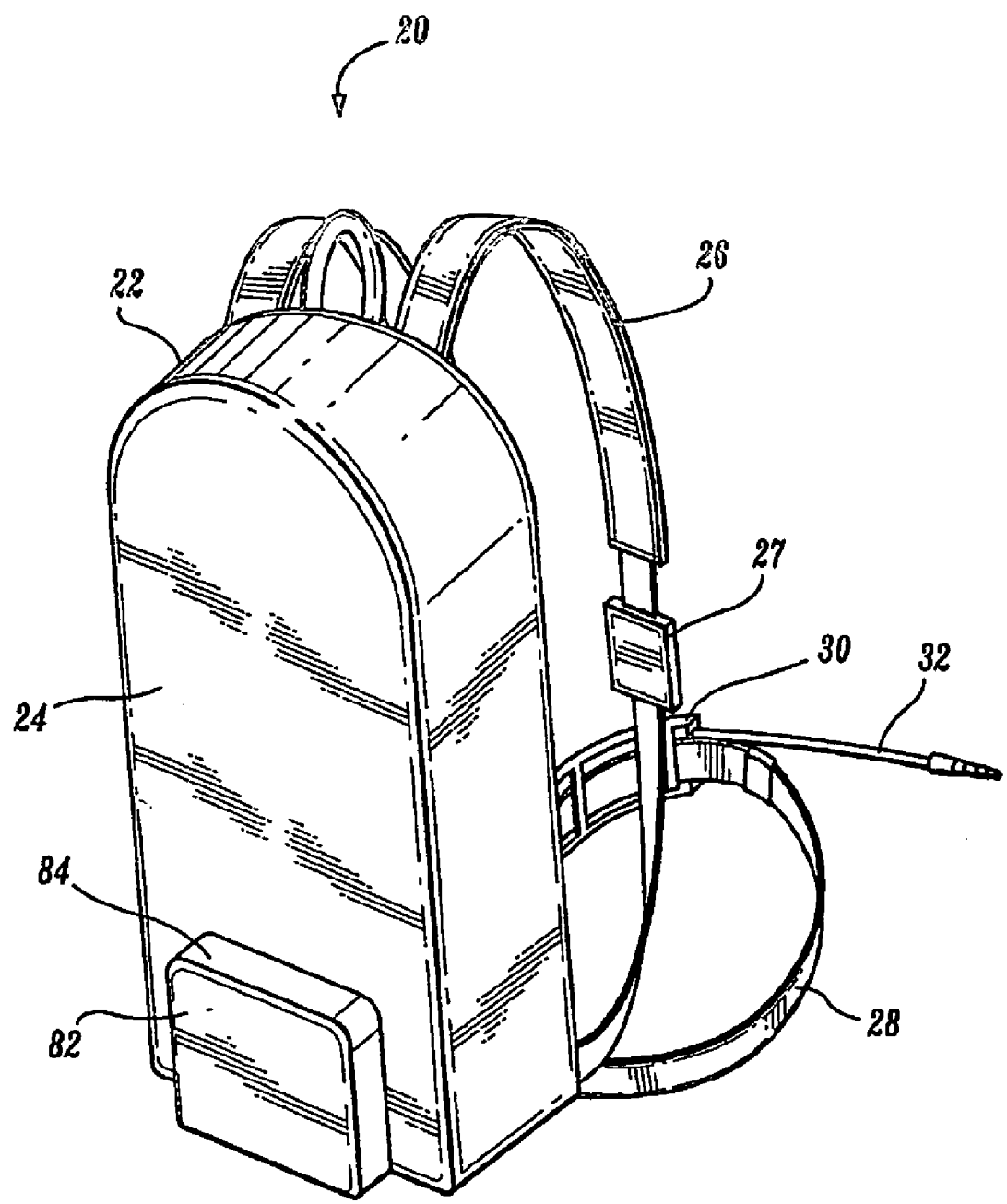
FIG. 1 is a perspective view of a portable enteral feeding apparatus and a belt apparatus, in accordance with the principles of the present disclosure.

The following discussion includes a description of the portable enteral feeding apparatus, in accordance with the principles of the present disclosure. Reference will now be made in detail to the exemplary embodiments of the disclosure, which are illustrated in the accompanying figures.

In the discussion that follows, the term "proximal" will refer to the portion of a structure that is closer to an enteral feeding apparatus, while the term "distal" will refer to the portion that is further from the enteral feeding apparatus. As used herein, the term "subject" refers to a patient.

Turning now to the figures, wherein like components are designated by like reference numerals throughout the several views, the exemplary embodiments of the portable enteral feeding apparatus and methods of use disclosed are discussed in terms of feeding apparatus for the enteral feeding of fluids to the body of a subject and more particularly, in terms of an enteral feeding apparatus that may be employed with alternately configured enteral feeding containers. An enteral feeding tube concealment belt adapted for use with the portable enteral feeding apparatus. The enteral feeding apparatus includes a removable pouch for supporting variously configured enteral feeding containers and a design that prevents kinking or damage to an enteral feeding tube. The enteral feeding apparatus substantially immobilizes components of an enteral feeding system relative to a subject thereby relieving strain on the feeding tube and preventing injury and irritation to the subject. It is envisioned that the present disclosure may be employed with a range of medical applications such as, for example, ambulatory dialysis, intravenous administration of fluids, etc. It is contemplated that the enteral feeding apparatus can be used for administration and/or removal of fluids such as, for example, medication, saline, bodily fluids such as, blood, urine, etc.

Referring initially to FIG. 1, an illustrative embodiment of a portable enteral feeding apparatus 20 is shown. The portable enteral feeding apparatus 20 includes a body 22 enclosed by a flap 24. Shoulder straps 26 are attached to body 22 for supporting portable enteral feeding apparatus 20 on a subject. A belt 28 is secured to body 22. Belt 28 is adjustable to comfortably fit around a subject's waist and substantially immobilize portable enteral feeding apparatus 20 against the subject. Belt 28 also supports a belt apparatus 30 that supports and conceals an enteral feeding tube 32.

Figure 2:
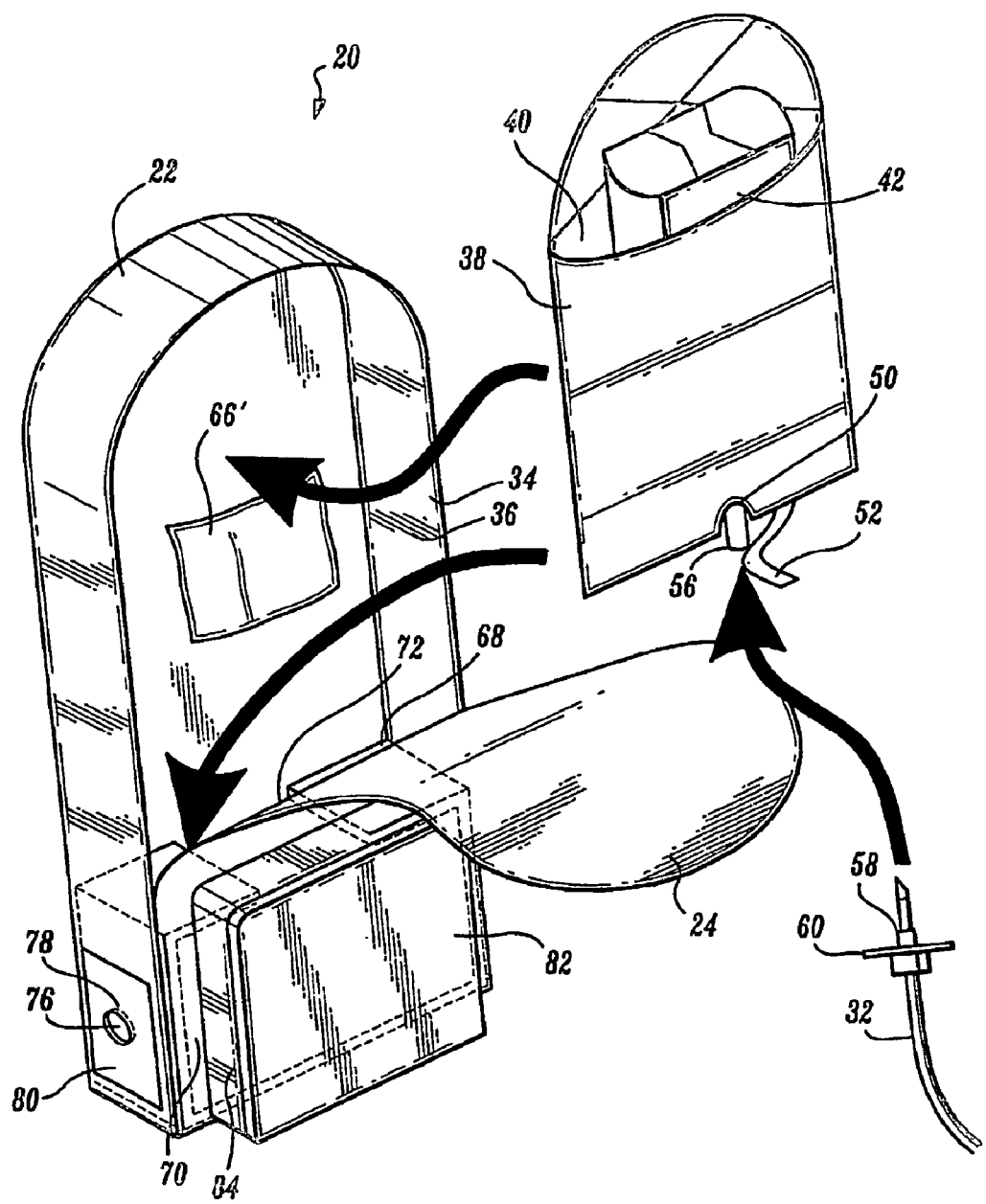
FIG. 2 is a perspective view of the portable enteral feeding apparatus shown in FIG. 1 with parts separated.
Figure 3:
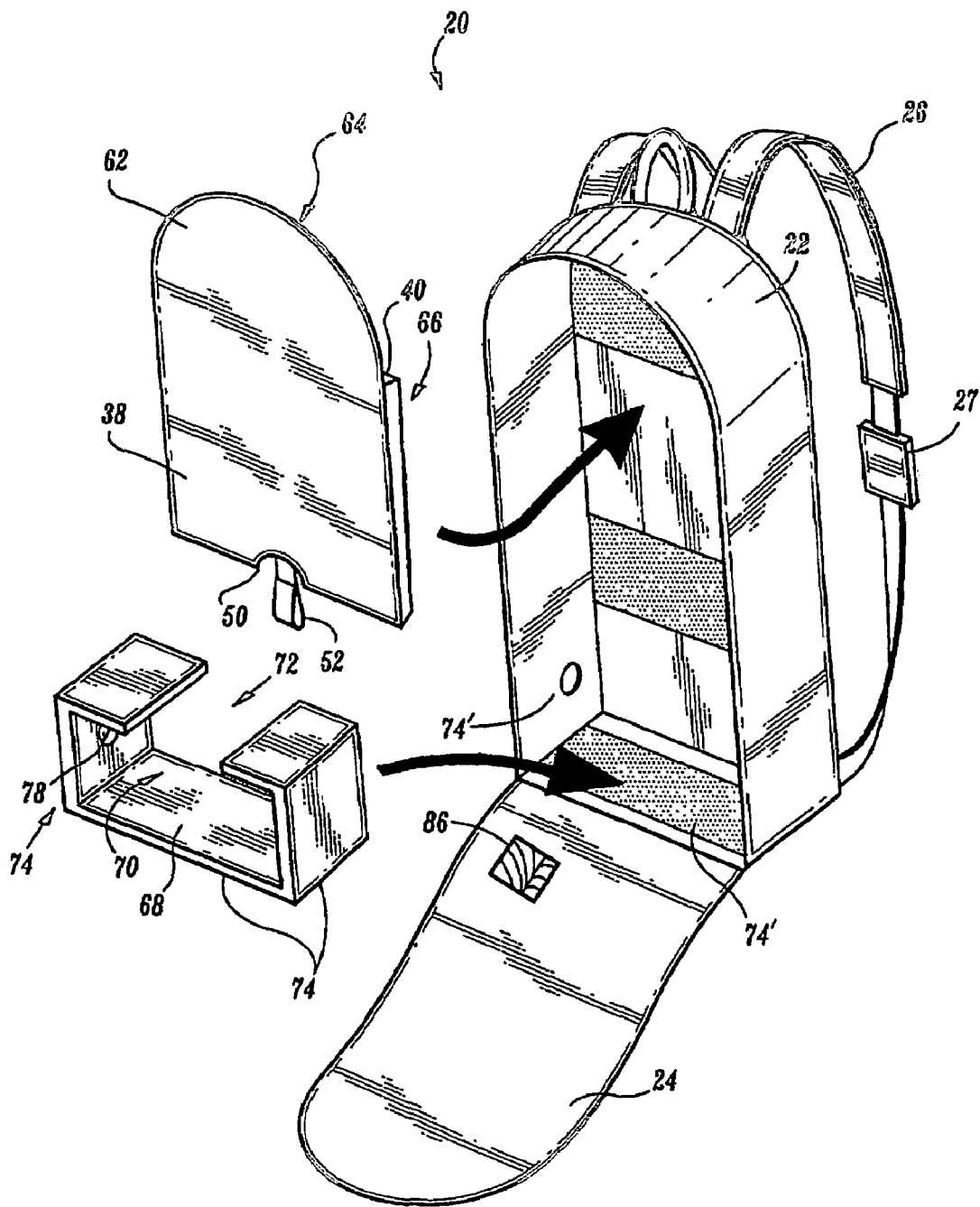
FIG. 3 is an alternate perspective view of the enteral feeding apparatus shown in FIG. 1 with parts separated.

Referring to FIGS. 2-3, portable enteral feeding apparatus 20 includes body 22 having flap 24 extending therefrom. Body 22 has an inner surface 34 that defines a cavity 36 such that flap 24 is movable to enclose cavity 36 of body 22. A pouch 38 is disposed within cavity 36 of body 22 and defines at least one compartment 40, as will be discussed. The compartment 40 is pliable and configured to support a fluid container, such as, for example, an enteral feeding container 42. Pouch 38 further defines an outer surface 44 that mounts to inner surface 34 of body 22. It is contemplated that pouch 38 may include one or a plurality of compartments 40. It is further contemplated that one or a plurality of the compartments 40 of pouch 38 may be pliable. Other compartments may be rigid, semi-rigid, etc. It is envisioned that enteral feeding container 42 may include nutritional, medicinal, etc. fluids for administration to a subject.

Inner surface 34 of body 22 defines a cavity 36. Cavity 36 is configured to support pouch 38. Cavity 36 may be variously configured and dimensioned according to the particular requirements of a fluid administration application.

Flap 24 of body 22 is moveable from an open position (FIGS. 2, 3) to a closed position (FIG. 1) to enclose cavity 36. Flap 24 is permanently attached to a portion of body 22, such as, for example, a bottom end of body 22. Flap 24 is removably attached to body 22 along its outer surface to enclose cavity 36 of body 22. Flap 24 is removably attached via a zipper or the like. Flap 24 may be alternatively removably attachable with the outer surface of body 22 via snaps, clips, etc. It is contemplated that flap 24 may be completely detachable from body 22.

Figure 4:
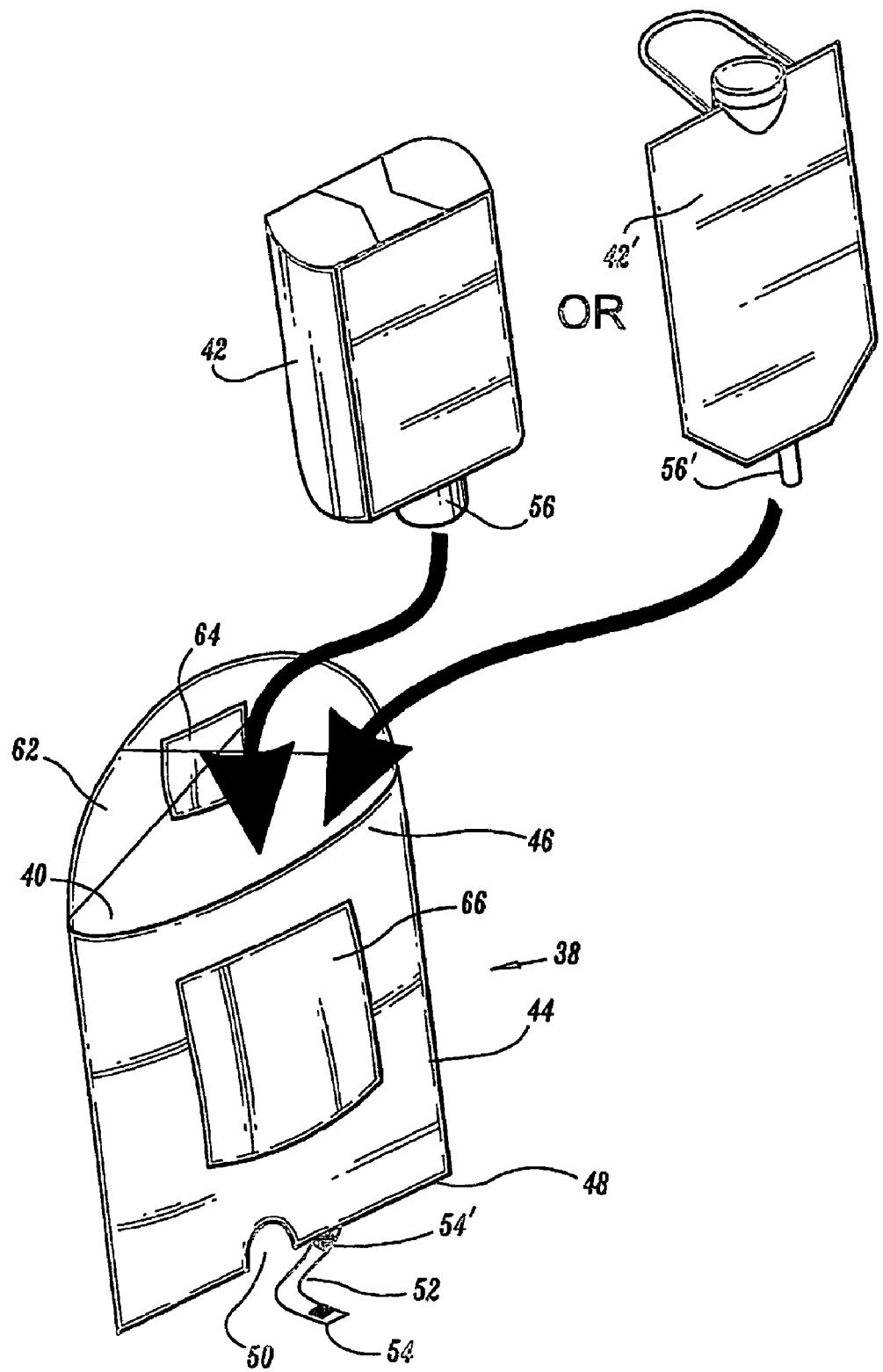
FIG. 4 is a perspective view of a pouch of the portable enteral feeding apparatus, shown in FIG. 1 with alternate enteral feeding containers removed therefrom.

Referring to FIG. 4, pouch 38 has an outer surface 44 and an inner surface that defines a compartment 40. Pouch 38 has a top end 46 that is substantially open to facilitate placement of enteral feeding container 42 within compartment 40. A bottom end 48 of pouch 38 is substantially closed to facilitate support of enteral feeding container 42.

An opening 50 is formed in bottom end 48. Opening 50 is configured for disposal of a portion, such as, for example, a neck 56, 56' of enteral feeding container 42 that connects to an enteral feeding tube 32, as will be discussed. Opening 50 may be variously configured and dimensioned to accommodate variously sized containers, according to the particular requirements of a feeding application.

A tube restraining strap 52 extends from bottom end 48 proximate to opening 50. Tube restraining strap 52 can be monolithically formed with pouch 38 or attached as a separate component by sewing, bonding, etc. A hook and loop patch 54 is mounted to a first end of tube retention strap 52 for releasable attachment with a cooperating hook and loop patch 54' mounted to a second end thereof. The attachable configuration of tube restraining strap 52 forms a loop for support of enteral feeding tube 32. This configuration advantageously immobilizes the portion of enteral feeding tube 32 disposed adjacent opening 50 to prevent kinking and strain on enteral feeding tube 32.

Alternatively, the cooperating hook and loop patch 54' may be mounted to outside surface 44 of pouch 38 to form a releasable loop. Hook and loop patches 54, 54' may include materials, such as, for example, Velcro®, etc. Other fasteners such as, for example, snaps, buttons, etc. can also be used.

Compartment 40 of pouch 38 is configured and dimensioned to receive variously configured fluid containers, such as, for example, a rigid enteral feeding container 42, a soft fluid container 42', etc. It is contemplated that compartment 40 may be configured to support one or a plurality of fluid containers.

Enteral feeding container 42 is rigid and has a neck 56 configured for attachment to enteral feeding tube 32. Attachment of enteral feeding container 42 with enteral feeding tube 32 facilitates fluid flow of nutrients, medicine, etc. to a subject. One end of enteral feeding tube 32 has a fitting 58 including a flange 60 for attachment to fluid container neck 56. Opening 50 is configured and dimensioned for placement of neck 56 when container 42 is disposed in pouch 38. Alternatively, a soft fluid container 42' may be placed within pouch 38. Soft fluid container 42' has a neck 56' configured for disposal within opening 50 and attachment to feeding tube 32.

Pouch 38 includes a flap 62 extending from top end 46. Flap 62 facilitates enclosure of compartment 40 and fluid containers supported therein. Referring also to FIGS. 2-3, flap 62 extends upwardly from top end 46 and includes a hook and loop patch 64 for releasable attachment to cooperating hook and loop patches mounted to inner surface 34 of body 22. Pouch 38 is disposed within body 22 such that flap 62 extends over open top end 46 to engage inner surface 34. This configuration advantageously encloses enteral feeding container 42 within pouch 38 and secures pouch 38 to body 22.

Hook and loop patch 64 may include materials, such as, for example, Velcro®, etc. and may be uniformly or non-uniformly configured. Other fasteners such as, for example, snaps, buttons, etc. can also be used. One or a plurality of hook and loop patches may be mounted to flap 62 and corresponding portions of inner surface 34. It is envisioned that flap 62 may removably attach to other portions of pouch 38 to enclose compartment 40. Removable attachment of flap 62 to inner surface 34 is not required.

Pouch 38 is mounted to body 22 by a hook and loop patch 66 mounted to outer surface 44 of pouch 38. Hook and loop patch 66 removably attaches to a cooperating hook and loop patch 66' mounted to inner surface 34 of body 22. Hook and loop patches 66, 66' facilitate removable attachment of pouch 38 with body 22. Hook and loop patches 66, 66' may include materials, such as, for example, Velcro®, etc. and may be uniformly or non-uniformly configured. Other fasteners such as, for example, snaps, buttons, etc. can also be used. One or a plurality of hook and loop patches 66, 66' may be employed and variously disposed about outer surface 44 of pouch 34 and inner surface 34 of body 22. Pouch 38 may alternatively be fixedly mounted with body 22.

A rigid support 68 is disposed adjacent a bottom end of cavity 36. Rigid support 68 defines a clearance space 70 and includes a gap defining a passageway 72. Passageway 72 facilitates communication between clearance space 70 and cavity 36. Hook and loop patches 74 are mounted to an outer surface of rigid support 68 for removable attachment to cooperating hook and loop patches 74' mounted to inner surface 34 of body 22. Removable attachment, via patches 74, 74' facilitates removal and placement of rigid support 68 within body 22. Hook and loop patches 74, 74' may include materials, such as, for example, Velcro®, etc. and may be uniformly or non-uniformly configured. Other fasteners such as, for example, snaps, buttons, etc. can also be used. One or a plurality of hook and loop patches 74, 74' may be employed and variously disposed about the surfaces of rigid support 30 and inner surface 34 of body 22.

An orifice 76 formed in body 22 is aligned with an opening 78 of rigid support 68 for disposal of enteral feeding tube 32. A hook and loop patch is mounted to an outer surface of body 22 about orifice 76. Hook and loop patch 80 may be aligned with orifice 76 for removable attachment to a cooperating hook and loop patch mounted with a belt apparatus 30 (FIGS. 5-10).

In one embodiment, portable enteral feeding apparatus 20 provides gravity assisted fluid flow without requiring a fluid pump to facilitate fluid flow from enteral feeding container 42, through enteral feeding tube 32, to a subject. In an ambulatory application, portable enteral feeding apparatus 20 includes pouch 38, maintained within body 22, that supports enteral feeding container 42 at an elevated level relative to the location where enteral feeding tube 32 enters a subject's body. Thus, gravity is advantageously employed to facilitate administration of nutrients, medicine, etc. to the subject.

Alternatively, a pump compartment flap 82 is removably attached along flap 24 to enclose a pump compartment 84. Pump compartment 84 is configured to support a pump that is operable with enteral feeding container 42 and enteral feeding tube 32 to facilitate administration of nutrients, medicine, etc. to the subject. One skilled in the art will realize pumps and related components suitable for fluid administration applications can be used in the portable enteral feeding apparatus in accordance with the present disclosure. Pump compartment 84 is disposed with a lower end of body flap 24.

Pump compartment flap 82 is removably attachable via a zipper or the like. Flap 82 may be alternatively removably attachable with the outer surface of body 22 via snaps, clips, etc. Pump compartment flap 82 is movable to an open position and a closed position of pump compartment 84. It is envisioned that portable enteral feeding apparatus 20 does not require use of a pump or related components.

A ductway 86 is disposed in flap 24 of body 22 to provide access between pump compartment 84 and clearance space 70 of rigid support 68. Feeding tube 32, which is disposed through orifice 76, is caused to communicate with a pump (not shown) via tubing, etc. through ductway 86. Ductway 86 communicates with pump compartment 84 and directs tubing, etc., communicating with feeding tube 32 therein. For example, an additional tubing section extends from the pump and through ductway 86 to clearance space 70. The tubing extending from the pump may attach to neck 56 of enteral feeding container 42 to facilitate flow of fluids through feeding tube 32. It is contemplated that a pump and related components may facilitate fluid flow of fluids as an alternative to gravity flow feeding or in addition to gravity flow feeding.

Adjustable shoulder straps 26 and shoulder strap buckles 27 are attached to body 22 for removably securing portable enteral feeding apparatus 20 to a subject and substantially immobilizing apparatus 20 relative to the subject.

The components of portable enteral feeding apparatus 20 can be fabricated from materials suitable for medical applications such as, for example, nylon, durable synthetic fiber materials, etc. Pouch 38 is pliable to accept variously configured enteral feeding containers and may be fabricated from suitable materials, such as, for example, flexible synthetic fiber materials, elastics, etc. Rigid support 68 can be fabricated from suitable materials, such as, for example, stainless steel, thermoplastic materials, etc. Body 22 may be fabricated from pliable materials, however, semi-rigid materials and rigid stiffeners may be incorporated therewith. One skilled in the art, however, will realize that other materials and fabrication methods suitable for assembly and manufacture of portable enteral feeding apparatus 20, in accordance with the present disclosure, also would be appropriate.

In use, enteral feeding container 42 is positioned in pouch 38 such that neck 56 of container 42 is accessible through opening 50. Rigid support 68 is removably attached, as discussed above, adjacent the bottom end of body 22. Opening 78 in rigid support 68 is aligned with orifice 76 in body 22. Passageway 72 in rigid support 68 provides access between neck 56 and clearance space 70. Pouch 38 is removably attached, as discussed above, to inner surface 34 of body 22 and supported on rigid support 68.

Feeding tube 32 is positioned through orifice 76 into clearance space 70. An end of feeding tube 32 is connected to neck 56 of feeding container 42. Feeding tube 32 is secured to neck 56 by engaging a fitting 58 to tube retention strap 52 extending from pouch 38. Flap 24 is disposed in the closed position. Portable enteral feeding apparatus 20 is securely mounted to a subject via adjustable shoulder straps 26 extending from body 22.

Enteral feeding tube 32 administers nutrients, medicine, etc. to the subject from enteral feeding container 42, as advantageously facilitated by portable enteral feeding apparatus 20. Portable enteral feeding apparatus 20 may employ gravity assisted fluid flow, pump assisted fluid flow, or a combination thereof, as discussed above. Other fluid administration applications of portable enteral feeding apparatus 20 are also contemplated, such as, for example, fluid collection.

Referring to FIGS. 5-10, a belt apparatus 30 is described for attachment to body 22 of portable enteral feeding apparatus 20 for support and concealment of enteral feeding tube 32. Belt apparatus 30 includes an extendable duct 92 that prevents kinking or damage to an enteral feeding 32 tube and prevents injury and irritation to the subject. It is contemplated that belt apparatus 30 may be designed for attachment to variously configured enteral feeding apparatus.

Belt apparatus 30 is adapted for use with portable enteral feeding apparatus 20 having enteral feeding tube 32 extending therefrom. Belt apparatus 30 includes belt 20 having a first end and a second end that are attachable with a buckle 88. It is contemplated that other fasteners may be used. A first member, such as, for example, stationary belt section 90 is supported with belt 28.

Figure 6:
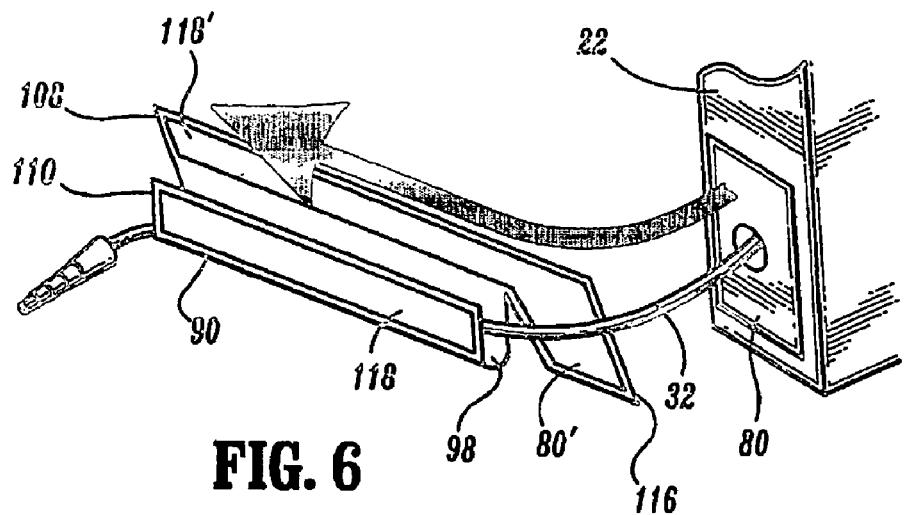
FIG. 6 is a perspective view of a portion of the belt apparatus shown in FIG. 5, illustrating a step for assembly.
Figure 7:
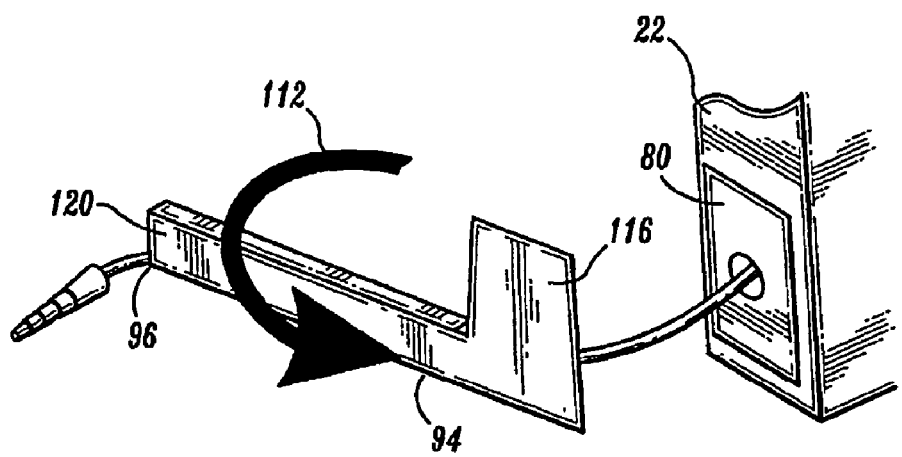
FIG. 7 is a perspective view of a portion of the belt apparatus shown in FIG. 5, illustrating another step for assembly.

A first end 94 of stationary belt section 90 is mountable to body 22 and a second end 96 is configured for disposal of enteral feeding tube 32 that is supported within cavity 98, as shown in FIGS. 6-7. It is envisioned that cavity 98 may variously configured to support varying sizes of enteral feeding tube 32 and/or other feeding apparatus. It is further envisioned that stationary belt section 90 may extend variable lengths according to the particular requirements of a feeding application.

Figure 8:
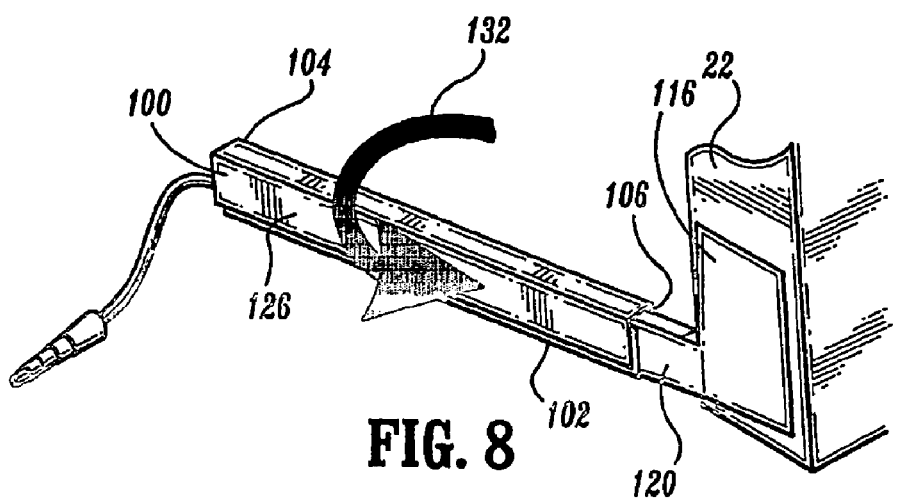
FIG. 8 is a perspective view of a portion of the belt apparatus shown in FIG. 5, illustrating another step for assembly.

A second member, such as, for example, telescoping belt section 100 has a first end 102 and a second end 104, as shown in FIG. 8. Telescoping belt section 100 defines a cavity 106 that supports stationary belt section 90 for movement of telescoping belt section 100 relative to stationary belt section 90. First end 102 of telescoping belt section 100 is configured for disposal of stationary belt section 90. Second end 104 of telescoping belt section 100 is configured for disposal of enteral feeding tube 32.

It is envisioned that cavity 106 may be variously configured to support varying sizes of stationary belt section 90 and/or other feeding apparatus. It is further envisioned that telescoping belt section 100 may extend variable lengths according to the particular requirements of a fluid administration application. It is contemplated that the first member may include a telescoping belt section and the second member may include a stationary belt section. It is further contemplated that the first member and/or the second member may include one or a plurality of belt sections.

The stationary belt section 90 as shown partially assembled in FIGS. 6-7 has an outer flap 108 and an inner flap 110. In an assembly step indicated by arrow 112, in the direction shown in FIG. 7, inner flap 110 is folded around enteral feeding tube 32 to form cavity 98 in which enteral feeding tube 32 is loosely disposed. Enteral feeding tube 32 may alternatively be closely fit with stationary belt section 90.

Stationary belt section 90 is fabricated from materials suitable for medical applications, such as, for example, nylon, multi-ply material such as, for example, a double layer nylon, etc., depending on the particular enteral feeding application and/or preference of a practitioner. Other suitable materials having a low coefficient of friction against similar nylon components to facilitate relative movement may also be used. One skilled in the art, however, will realize that other materials and fabrication methods suitable for assembly and manufacture, in accordance with the present disclosure, also would be appropriate.

Figure 9:
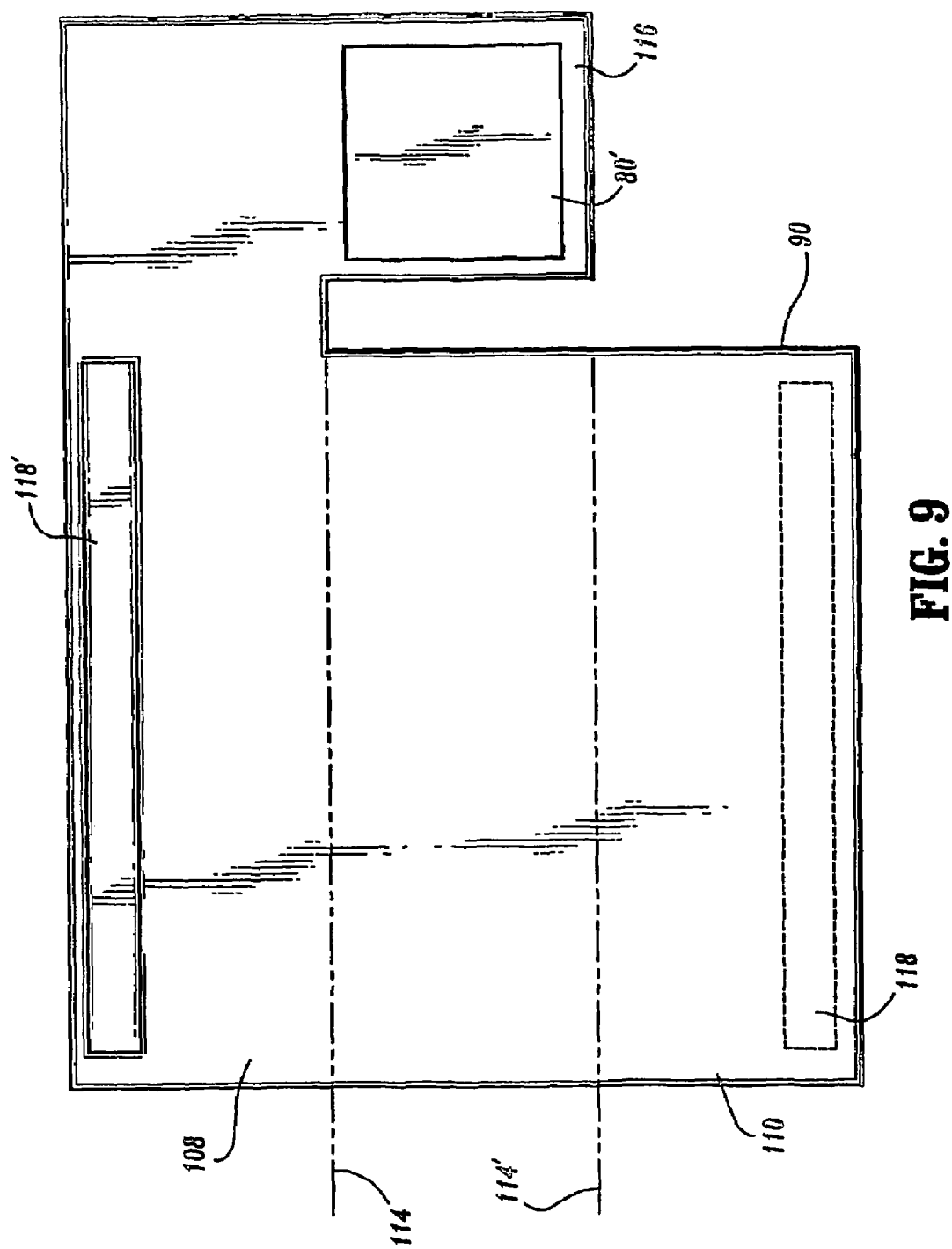
FIG. 9 is a front orthographic view of a disassembled first belt section.

Folding lines 114 and 114' are represented in phantom. Permanent creases may be maintained at the folding lines, for example, by providing stitching at the folding lines for easily forming ducts having a rectangular cross-section, as shown in FIG. 9. Alternative embodiments provide rounded cross-section ducts without requiring any permanent creases or crease stitching.

A concealment flap 116 extends from outer flap 108 of stationary belt section 90. Concealment flap 116 is formed by forming a transverse cut at the proximal end of inner flap 110. Concealment flap 116 supports a fastener for connection to a mating fastener on body 22. Fastener and mating fastener include cooperating hook and loop strips 80, 80' (see FIGS. 6-8) to facilitate releasable attachment of concealment flap 116 with body 22. Hook and loop strips, such as, for example, Velcro®, etc. or other fasteners such as, for example, snaps, buttons, etc. may be used to connect stationary belt section 90 to body 22.

A hook and loop strip 118 is disposed along a back edge of inner flap 110. A cooperating hook and loop strip 118' is disposed along a front edge of outer flap 108. In an assembly step indicated by arrow 112 in the direction shown in FIG. 7, outer flap 108 of stationary belt section 90 is folded over inner flap 110 and enteral feeding tube 32 to form a stationary duct section 120 enclosing enteral feeding tube 32 therein. Hook and loop strips 118 and 118' are fastened together to attach outer flap 108 to inner flap 110 and thereby maintain the stationary duct 120 configuration. It is envisioned that many other fastener types, such as, for example, buttons, snaps, etc. can be used to attach outer flap 108 to inner flap 110.

Hook and loop strips 118 and 118' are attached, typically by sewing, along the back edge of inner flap 110 and front edge of outer flap 108. Alternatively, hook and loop strips can be attached to suitable materials using adhesives. In the illustrative embodiment, hook and loop strip 118' on outer flap 108 is monolithic with hook and loop patch 80' on the concealment flap 116. This configuration advantageously simplifies manufacture. It is envisioned that hook and loop strip 118', or portions thereof, and hook and loop patch 80', or portions thereof, may be separate and integrally connected.

Stationary duct section 120 is attached to body 22 by engaging fastener such as, for example, hook and loop patch 80' on concealment flap 116 with fastener such as, for example, hook and loop patch on body 22. Slack in enteral feeding tube 32 is taken up by sliding enteral feeding tube 32 distally through stationary duct section 120 as the proximal end of stationary belt section 90 is moved toward body 22.

Figure 10:
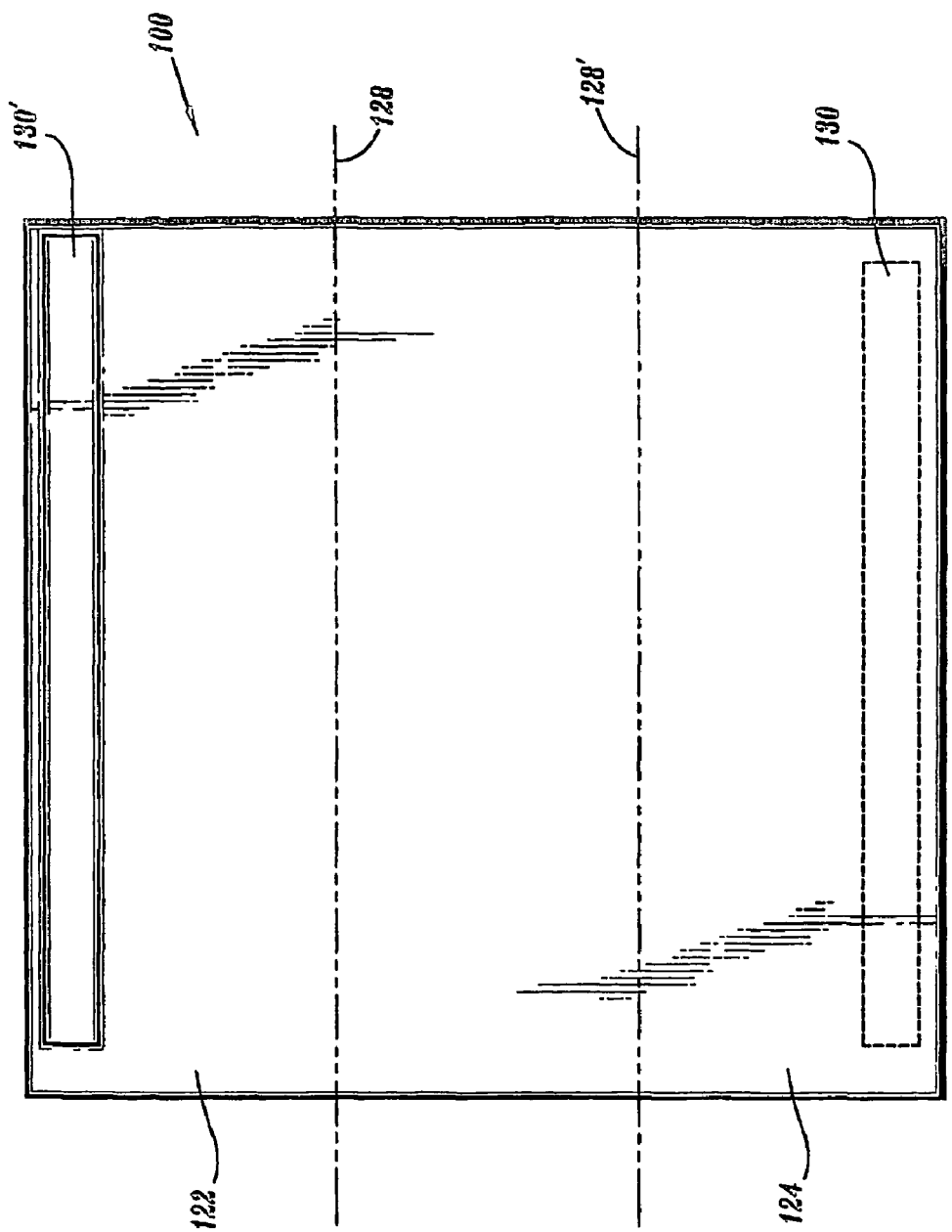
FIG. 10 is a front orthographic view of a disassembled second belt section.

Telescoping belt section 100 has an outer flap 122 and an inner flap 124, as shown in FIGS. 8 and 10. Telescoping belt section 100 forms a telescoping duct section 126 disposed loosely around the outside of stationary duct section 120. Telescoping belt section 100 may alternatively be closely fit with stationary belt section 90.

Telescoping belt section 100 is fabricated from materials suitable for medical applications, such as, for example, nylon, multi-ply material such as, for example, a double layer nylon, etc., depending on the particular enteral feeding application and/or preference of a practitioner. Other suitable materials having a low coefficient of friction against similar nylon components to facilitate relative movement may also be used. One skilled in the art, however, will realize that other materials and fabrication methods suitable for assembly and manufacture, in accordance with the present disclosure, also would be appropriate.

Folding lines 128 and 128" are represented in phantom. Permanent creases may be maintained at the folding lines, for example, by providing stitching at the folding lines to easily form ducts having a rectangular cross-section. Alternative embodiments provide rounded cross-section ducts without requiring any permanent creases or crease stitching.

A hook and loop strip 130 is disposed along a back edge of inner flap 124 and a mating hook and loop strip 130' is disposed along a front edge of outer flap 122. In an assembly step indicated by arrow 132 in the direction shown in FIG. 8, telescoping belt section 100 is formed by first folding inner flap 124 around stationary duct section 120. Outer flap 122 is folded about stationary duct section 120 and inner flap 124. Outer flap 122 is secured to inner flap 124 by fastening together hook and loop strips 130 and 130' to maintain the telescoping duct 126 configuration. It is envisioned that other fastener types such as, for example, buttons, snaps, etc. can be used in place of hook and loop strips 130 and 130'.

One end of belt 28 (see FIG. 5) is drawn between telescoping belt section 100 and stationary belt section 90 and exits adjacent ends of stationary belt section 90, telescoping belt section 100, respectively. Belt 28 is thereby disposed in cavity 106, between telescoping belt section 100 and stationary belt section 90. Belt 28 is positioned about and secured to a subject (not shown) by attaching the first and second ends thereof with buckle 88.

The subject may use portable enteral feeding apparatus 20 with support for enteral feeding tube 32 provided by belt apparatus 30 for ambulatory, portable, etc. applications. In an alternative embodiment, stationary belt section 90 and telescoping belt section 100 include external belt loops (not shown) for disposing a waist belt. In still another embodiment, loops (not shown) extending from body 22 are provided for supporting belt sections 90, 100 and/or belt 28.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A telescoping feeding tube concealment belt apparatus adapted for use with an enteral feeding device having tubing extending therefrom, the belt apparatus comprising:
a belt having a first end and a second end that are attachable;
a first member having an first flap and a second flap and a concealment flap, the first flap having at a least one folding line that folds around the second flap to form a cavity in the first member for locating tubing exiting the device, a second member having a first flap and a second flap, the second flap having at least one folding line that folds around the first flap to form a cavity in the second member for locating the first member, and a first end of the second member is configured for locating the tubing exiting the cavity of the first member, the second member forms its cavity slightly larger than the first member, wherein the second member is extended or retracted relative to the first member by sliding the second member over the first, the concealment flap being releasably attachable to an outside portion of a body for concealing the tubing exiting the device.

2. An apparatus according to claim 1 wherein said first member and said second member are attached to the belt via belt-loops disposed on an outside surface of said first and second members.

3. An apparatus according to claim 1 wherein said body includes an orifice disposed therein for locating a proximal end of said tubing.

* * * * *